Figures 4, 5:
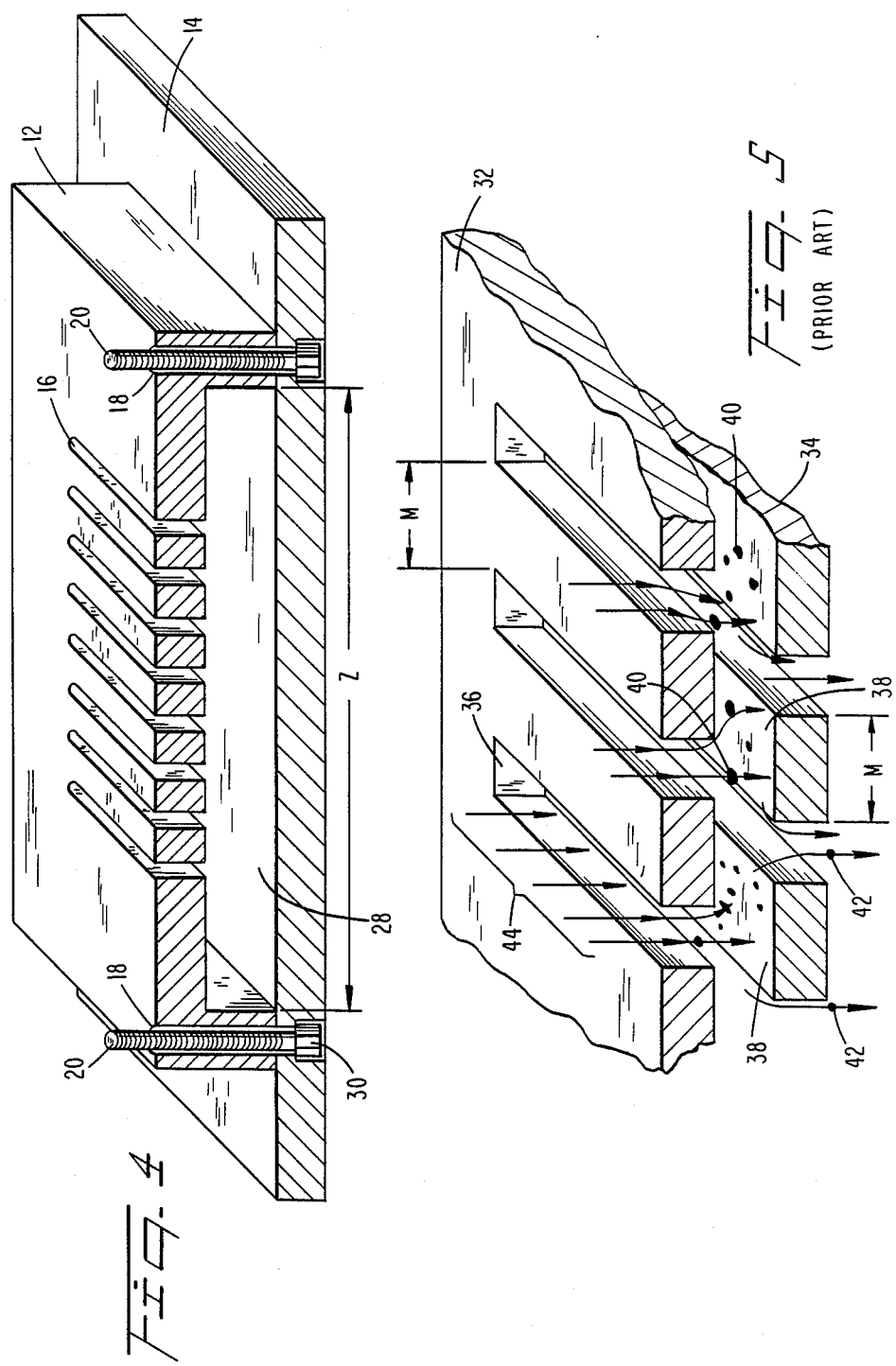

United States Patent [19]

Langer

[11] Patent Number: 4,764,186

[45] Date of Patent: Aug. 16, 1988

[54] PARTICLE IMPACTOR ASSEMBLY FOR SIZE SELECTIVE HIGH VOLUME AIR SAMPLER

[75] Inventor: Gerhard Langer, Boulder, Colo.

[73] Assignee: The United States of America as represented by the United States Department of Energy, Washington, D.C.

[21] Appl. No.: 28,981

[22] Filed: Mar. 23, 1987

[51] Int. Cl.$^4$ ............................................. B01D 57/00
[52] U.S. Cl. ......................................... 55/17; 55/270; 55/277; 55/443; 73/28
[58] Field of Search ...................... 55/17, 97, 270, 277, 55/319, 320, 442-446; 73/28

[56] References Cited

U.S. PATENT DOCUMENTS

| | | | |
|---|---|---|---|
| 1,767,089 | 6/1930 | Miller et al. | 55/446 X |
| 3,518,815 | 7/1970 | McFarland et al. | 55/241 |
| 3,681,973 | 8/1972 | Ludwig | 73/28 |
| 4,038,057 | 7/1977 | Roth | 55/270 |
| 4,159,196 | 6/1979 | Schneider et al. | 55/444 X |
| 4,189,937 | 2/1980 | Nelson | 73/28 |
| 4,211,116 | 7/1980 | Pilat et al. | 73/421.5 A |
| 4,274,846 | 6/1981 | Smith | 55/270 |
| 4,321,822 | 3/1982 | Marple et al. | 73/28 |
| 4,461,183 | 7/1984 | Wedding | 73/863.21 |
| 4,557,739 | 12/1985 | Fortman et al. | 55/320 |

OTHER PUBLICATIONS

Langer, "Evaluation of PM-10 Commercial Inlets for New Surveillance Air Sampler", Semi-Annual Report, Published as Part of RFP 4036, Rocky Flats Plant, (07/85-12/85), Print Date: 5/87, Distribution Date: 6/87.

Primary Examiner—Charles Hart
Attorney, Agent, or Firm—Anne D. Daniel; James H. Chafin; Judson R. Hightower

[57] ABSTRACT

Air containing entrained particulate matter is directed through a plurality of parallel, narrow, vertically oriented impactor slots of an inlet element toward an adjacently located, relatively large, dust impaction surface preferably covered with an adhesive material. The air flow turns over the impaction surface, leaving behind the relatively larger particles according to the human thoracic separation system and passes through two elongate exhaust apertures defining the outer bounds of the impaction collection surface to pass through divergent passages which slow down and distribute the air flow, with entrained smaller particles, over a fine filter element that separates the fine particles from the air. The elongate exhaust apertures defining the impaction collection surface are spaced apart by a distance greater than the lengths of elongate impactor slots in the inlet element and are oriented to be normal thereto. By appropriate selection of dimensions and the number of impactor slots air flow through the inlet element is provided a nonuniform velocity distribution with the lower velocities being obtained near the center of the impactor slots, in order to separate out particles larger than a certain predetermined size on the impaction collection surface. The impaction collection surface, even in a moderately sized apparatus, is thus relatively large and permits the prolonged sampling of air for periods extending to four weeks.

20 Claims, 3 Drawing Sheets

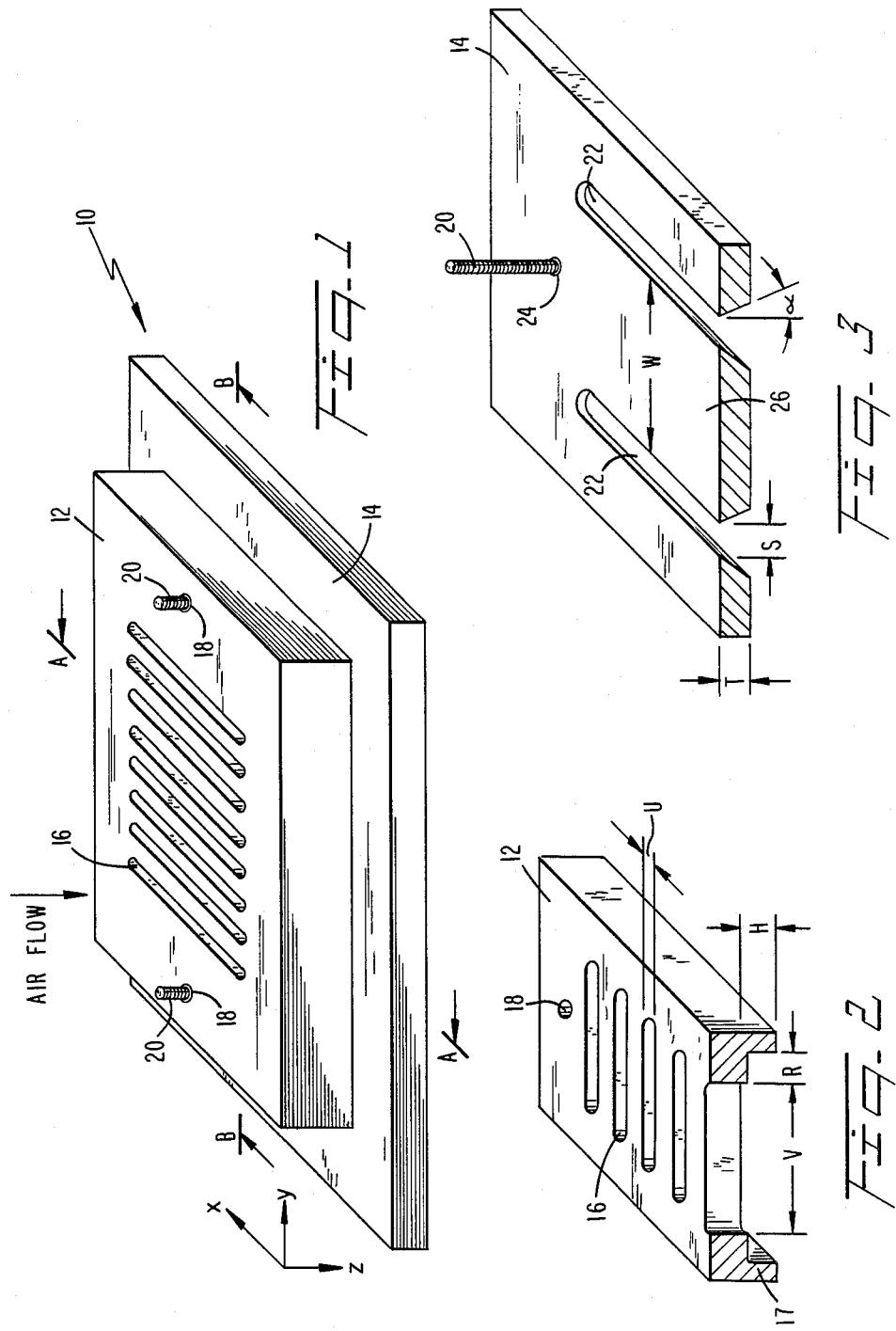

U.S. Patent  Aug. 16, 1988  Sheet 2 of 3  4,764,186

PARTICLE IMPACTOR ASSEMBLY FOR SIZE SELECTIVE HIGH VOLUME AIR SAMPLER

The U.S. Government has rights in this invention pursuant to contract No. DE-AC04-76DP03533 between the U.S. Department of Energy and Rockwell International Corporation.

BACKGROUND OF THE INVENTION

1. Field of the Invention

This invention relates generally to surveillance air samplers for sampling particulates in ambient air, e.g., to demonstrate local compliance with EPA PM-10 regulations by municipalities and industry, and, more particularly, to an improved particle impactor assembly for size selective fractionating of particulates collected over long periods of time in high volume air samplers.

2. History of the Prior Art

Surveillance air samplers are widely used to monitor particulate air pollution, in aerosol research studies in general, and for safety monitoring in the vicinity of industrial plants that process radioactive materials. Government agencies, especially the United States Environmental Protection Agency (EPA, hereinafter) specify various particulate sampling criteria, generally formulated in terms of the effective aerodynamic diameter of the collected particulates in air flow passed through an air sampler. Likewise, the U.S. Department of Energy (DOE, hereinafter) has also enacted guidelines for DOE licensed nuclear facilities, e.g., 40 CFR 61, part H, due to the highly stringent health considerations for airborne radio nucleides.

In 1984, the EPA developed tentative PM-10 (less than 10 micron particle diameter) criteria for sampling the hazardous fraction of airborne dust, to regulate pollution that comprises particles small enough to be readily deposited in the human respiratory system. The aforementioned DOE guidelines, however, are also concerned with the recovery of particles larger than 10 micron diameters for analysis.

As persons skilled in the art will appreciate, all conventional air samplers include elements, e.g., screens, to keep out airborne insects, relatively large particles blown about during stormy weather, water in the form of raindrops or snowflakes, and the like. Basically, such conventional air samplers convey the air, after such jetsam has been extracted, generally through a plurality of apertures in an inlet element, to an impactor surface substantially normal to the particulate-laden air flow or to a cyclone for collection of particles for subsequent analysis. The smallest particles are typically captured on a fine filter surface.

For many analytical purposes, it is highly desirable to have at least the fine particulate matter fairly uniformly distributed over the filter element for X-ray analysis.

It is also known to apply a sticky coating, e.g., a thin layer of a substance such as petrolatum, commercially available as Vaseline (TM), on the impacted surface to capture the larger particles which otherwise may tend to bounce off. Successive collection stages are often utilized in the process to fractionate the particles by size.

U.S. Pat. No. 4,461,183, to Wedding, discloses an aerosol sampler inlet structure with performance characteristics that allow collection of particles small enough to be inhaled by humans (those having aerodynamic diameters less than 10 microns) independent of the sampling conditions of wind speed and direction.

U.S. Pat. No. 4,321,822, to Marple et al, and U.S. Pat. No. 4,211,116, to Pilat et al, are two examples of multi-stage sampling apparatuses in which different stages capture particles in different size ranges. The Marple et al apparatus includes an element in which apertures ara disposed in spiral configurations, with the impacted surface rotated adjacent thereto so that the deposit of collected dust is essentially uniformly distributed.

U.S. Pat. No. 3,518,815, to McFarland et al, discloses an apparatus in which particulate-laden air is provided through a plurality of elongate slots to a rotating impactor surface.

U.S. Pat. No. 4,038,057, to Roth discloses a closed circuit air sampler in which air is conveyed through pluralities of radially disposed apertures to an impactor surface enclosed in a frangible container, so that removal of the deposited dust requires destruction of the other structure to prevent reuse and possible contamination, deliberate or accidental, in successive uses of the device.

U.S. Pat. No. 3,681,973, to Ludwig, discloses a sampler structure mounted for rotation in a plane perpendicular to the wind direction and having an entrance slot communicating with a hollow aerodynamically shaped chamber lined at its internal surface with a collection paper for collecting the particles along the length thereof, the impingement points of differently sized particles being determined by the trajectories that the particles follow within the chamber, depending on a combination of wind speed, particle diameter, and centrifugal force related to the speed with which the sampler slot is rotated.

Although known air samplers typified by the ones discussed above are capable of separating particulates in the below 10 micron range from those that are larger, they are expensive, complicated to operate, pose problems in handling of the separate collection elements, and do not allow long term operation, e.g., for periods extending for up to four weeks at a time.

There is, therefore, a long felt and serious need for an improved surveillance air sampler for sampling ambient air for long periods of time, which is relatively inexpensive and easy to operate, which is readily adaptable to separate particles having aerodynamic diameters larger than 10 microns from those that are smaller, and which allows for easy recovery of both fractions.

SUMMARY OF THE INVENTION

Accordingly, it is an object of this invention to provide an improved particle impactor assembly, suitable for use with conventional air sampling apparatuses, for size selective collection of particulate matter entrained in the sampled air.

It is another object of this invention to provide an improved particle impactor assembly, suitable for use with conventional air sampler apparatuses, that will permit air sampling over a number of weeks.

It is a further object of this invention to provide an improved particle impactor assembly that is readily adapted to separate out particles of predetermined size from those that are smaller, during long duration sampling of particulate laden air.

It is an even further object of this invention to provide an improved particle impactor assembly suitable for use with a size selective, high volume, long duration air sampling operation that allows effective collection and recovery of particles up to 70 microns aerodynamic diameter.

It is also an object of this invention to provide a method for fractionating by size the collection of airborne particulate matter from air sampled over long periods of time by controlling the velocity distribution of the sampled air directed at a dust collecting impactor surface.

These and other related objects of this invention are achieved, in a preferred embodiment, by directing the air flow in an air sampler apparatus through a particle impactor assembly having an inlet element with a flat horizontal upper portion with a plurality of similar parallel slot-like inlet apertures, referred to hereinafter as impactor slots, each of which has a length V and width U. The inlet element also has a downwardly depending rim of height H. A flat impactor plate is sealingly affixable to the inlet element of this rim, and has in it a pair of similar parallel slot-like exhaust apertures having a width S, oriented normal to the impactor slots thereabove. At the upper surface of the impactor plate the exhaust apertures each have a length that extends past the last adjacent inlet slot by a distance of at least 2U. The rim portions of the inlet element that parallel the ends of the impactor slots are at a distance R therefrom, and at the upper surface of the impactor plate the exhaust apertures are separated by a distance of at least (V+2U). This geometry causes collection on the impactor plate of particles larger than 5 um with increasing efficiency, e.g. 50% efficiency at 10 um, the smaller particles tending to flow with the air passing through the exhaust apertures for separate filtration. In one aspect of this preferred embodiment, the exhaust apertures have diverging sides that slow down and distribute the flow to allow evenly distributed collection of the finer particles on a fine filter disposed therebelow.

Still other objects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modification in various obvious respects, all without departing from the invention as disclosed herein. Accordingly, the drawings and description of the invention are to be regarded as illustrative in nature, and not as restrictive.

DESCRIPTION OF THE DRAWINGS

FIG. 1 is a perspective view of the inlet element located above the impactor plate in the apparatus of the present invention. An x-y-z Cartesian reference system is provided for the convenience of subsequent reference.

FIG. 2 is a vertical cross sectional view of the inlet element at section A—A, i.e., in the x-z plane.

FIG. 3 is a vertical cross sectional view of the impactor plate at section A—A, i.e., in the x-z plane.

FIG. 4 is a vertical cross sectional view of the inlet element in position above the impactor plate at section B—B, i.e., in the y-z plane.

FIG. 5 is a vertical cross sectional view of portions of an inlet element and an impactor plate, in normally operative juxtaposition, as taught in the prior art, in the y-z plane.

FIG. 6 is a vertical cross sectional view, in the x-z plane, of the particle collecting elements according to a preferred embodiment of this invention.

DESCRIPTION OF THE PREFERRED EMBODIMENT

The present invention is intended to provide improved results in the operation of known air sampling apparatuses over prolonged periods, and, especially, for the separation thereby of airborne particles into two size fractions according to the human thoracic particle size separation at a nominal 10 micron aerodynamic diameter. This cut is different than the much sharper cut produced by a conventional impactor set at a 10 micron cut-point. It is to be understood that the normal practice of ensuring the elimination of flying insects, uninteresting and undesired jetsam, and water is obtained by conventional means. The particle-laden air that passes through the combination of the preferred embodiment of this invention likely will be flowing at a rate within a predetermined range, e.g., approximately 40 cfm or an impactor slot velocity of approximately 13 ft/s (4 m/s); over prolonged periods.

Referring now to FIG. 1, it should be noted that a reference Cartesian coordinate system is indicated by the triad x-y-z aligned with the principal sides of the generally rectangularly shaped elements illustrated therein.

The assembly 10 of FIG. 1 illustrates, in perspective view, an inlet element 12 placed on the upper surface of impactor plate 14. Purely for reference purposes, the longer sides of inlet element 12 and impactor plate 14 are aligned with the y axis and their respective widths are aligned with the x axis. Inlet element 12 is provided with a plurality of elongate impactor slots 16 through which air passes in a downward, i.e., z axis, direction. Inlet element 12 is also provided with two cylindrical apertures 18 through which are passed threaded bolts 20 used with washers and nuts (not shown) to affix together inlet element 12 and impactor plate 14 at a common contact plane. Thus, any air flowing downward through impactor slots 16 must pass through the two exhaust apertures (to be described hereinafter) provided in the impactor plate therebelow.

As illustrated in FIG. 2, inlet element 12 has a generally planar upper surface provided with similar elongate impactor slots 16 which are oriented to be parallel to each other. These are conveniently formed by a milling operation that causes their ends to be rounded cylindrically. The exact shape of the ends of impactor slot 16 is not critical to successful operation of the present invention. Impactor slots 16 in the preferred embodiment all have the same width U and same length V and are oriented to be in the x-z plane. Depending downwardly from the planar top portion of inlet element 12 by a distance H is a rim 17 around the periphery of inlet element 12. The inner vertical wall surfaces of rim 17 in the x-z plane are preferably parallel to each other and are separated by a distance R with respect to both ends of impactor slots 16. Thus, the separation between the inner vertical surfaces of rims 17 in the x direction is (V+2R). It is believed that for collection of particles in the range 10–70 microns the distance R should be not less than the width U of impactor slots 16. The height H of the rim 17 with respect to the lower surface of the upper planar portion of inlet element 12 is likewise a design parameter, just like the dimensions U, V and R, and all of these dimensions may be altered to suit the precise needs to be met by the overall air sampling system.

As best seen in FIG. 3, impactor plate 14 is a generally planar element at least as large in size as inlet element 12 at their common contacting surface and is provided with two elongate slot-like exhaust apertures 22 oriented to be in the y direction with respect to the reference coordinate system. In other words, exhaust apertures 22 are normal to impactor slots 16. Impactor plate 14 is provided with cylindrical apertures 24 through which are passed bolts 20. Each exhaust aperture 22 at the upper surface (at which contact is made with the inlet element 12) has a width S and the adjacent edges of parallel exhaust apertures 22 are separated by a distance W, which equals (V+2U).

Each of the exhaust apertures 22 has a length that preferably extends past the last adjacent impactor slot 16 by a distance at least twice the impactor slot width U, i.e. 2U, and is preferably formed to have sloping sides so that the exhaust aperture offers a diverging air passage in the downward or streamwise direction. Since the air flow through the exhaust apertures 22 is in the subsonic region under all operating conditions, such a divergence of the air flow passage through exhaust apertures 22 will cause the air flow to diverge laterally and simultaneously slow down. The consequences of this are discussed more fully hereinafter. Each of the sloping sides of exhaust apertures 22 preferably forms an angle $\alpha$ with the local vertical as shown in FIG. 3.

The heads of bolts 20 are located in recesses provided therefor in impactor plate 14. As shown in FIG. 4, planar contact between the upper surface of impactor plate 14 and rim 17 of inlet element 12 defines a collection surface 28 which in the y direction has the dimension Z. Although not clearly visible in FIG. 4, both of the exhaust apertures 22 are positioned below and symmetrically parallel to the plane passing through the axes of bolts 20 as well as the midpoints of impactor slots 16 thereabove.

FIG. 5 is an illustrative depiction of a known inlet-/impactor plate assembly, in vertical cross section normal to the impactor slots 36 of an inlet element 32 positioned parallel to and separated from an impactor plate element 34 having a plurality of elongate surfaces 38 that are impacted by particles and where some of the particles are collected.

Figure 6:
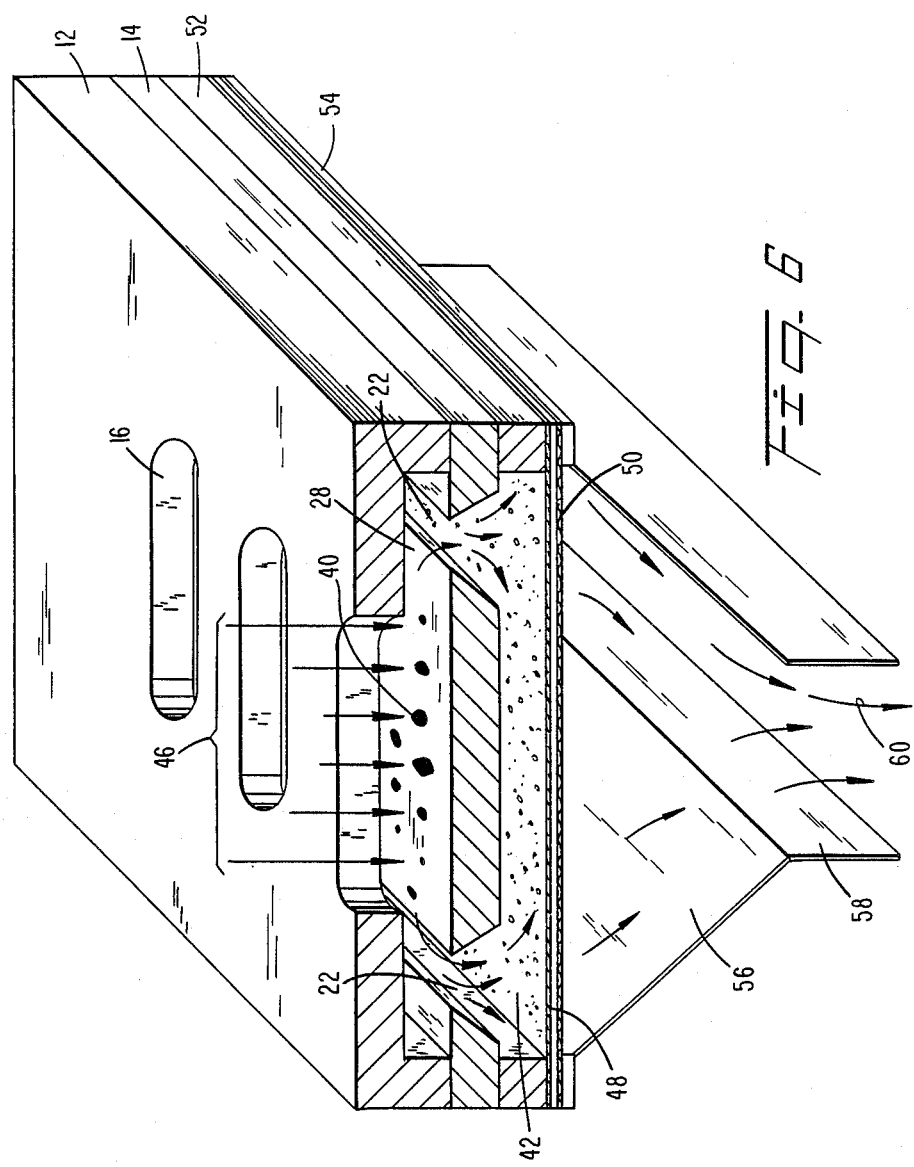

The principal components that work together and provide the improvement according to a preferred embodiment of this invention are best seen in FIG. 6. For convenience, impactor plate 14 and inlet element 12 are indicated as having the same outside dimensions of length and width in this figure. Persons skilled in the art will naturally be able to contemplate, design and utilize elements as taught in this disclosure regardless of the important dimensions of the contacting elements. Starting from the top, inlet element 12 contacts the top surface of impactor plate 14 which, in turn, contacts the top surface of a peripheral spacer element 52. Directly beneath spacer element 52 and in contact therewith is a thin, usually rather fragile, typically fiberglass paper-like filter element 48 resting on and supported by a fine wire screen 50 that is conveniently made of stainless steel. The outer edges of filter element 48 and screen 50 are sandwiched between the lower surface of spacer element 52 and the upper periphery of a tapered guide element 54 that has two long sides having tapered positions 56 and vertically oriented portions 58 to guide the air flow after the dust particles have been extracted therefrom by impaction collection of larger (typically more than 5 micron) particles on impactor plate 14 and the finer particles on filter element 48.

The essential geometry having been explained, it now becomes possible to explain the reasons for and the benefits obtained by the particular configurations selected for the various elements of the present invention. For this purpose, it is helpful to compare the known geometry illustrated in FIG. 5 and the improved geometry according to a preferred embodiment of the present invention as illustrated in FIG. 6. Note that the air flow downward through impactor slots 36 of the prior art (FIG. 5) has an essentially uniform velocity distribution along the length of each elongate impactor slot 36. This is indicated by downwardly directed equally sized arrows collectively identified by the numeral 44 in FIG. 5. The dust collecting areas 38 of impactor plate 34 of the prior art are disposed to be directly beneath corresponding impactor slots 36 and are relatively narrow, the distance between successive openings, i.e. exhaust apertures 35, on impactor plate 34 being characterized by the letter M. This is the same spacing as between adjacent impactor slots 36.

As a direct consequence of this selection of relative dimensions, the relatively uniform velocity distribution 44 of the particulate laden air flow through each impactor slot 36 corresponds to dust collection on one of the surface areas 38 having a width M directly therebelow. Relatively large and heavy dust particles 40 hit surface 38 and, in most instances, are collected thereon. The flow of air, however, has to divert to each side of each surface 38 to pass through the exhaust apertures 35 of impactor plate 34. This diversion of the air flow direction causes a centrifugal force further tending to throw the larger particles 40 toward impactor collection surface 38, but the samller dust particles 42 are light enough to follow the streamlines of the air flow and substantially pass between adjacent collection surface strips 38, as indicated by arrows pointed downward in FIG. 5. Experience has shown that the provision of a relatively uniform velocity distribution 44 through impactor slots 36, causes a sharp cut-off for the collection of particles larger than 10 microns, for example, instead of the more gradual rejection of particles near 10 microns, so that the desired fractionating effect of separating out particles larger than those that are likely to enter the human respiratory system is not adequately realized. The relatively narrow collection surfaces 38 can cause insufficient capture of larger particles, because proper, routine adhesive application to hold the large particles is difficult. Also particle recovery is impeded by the discontinous surfaces 38. Additionally, the narrow collection surface has a limited dust holding capacity of days versus a month.

By contrast to the prior art as illustrated in FIG. 5 and explained in the immediately preceding paragraph, as best understood with reference to FIG. 6, the preferred embodiment of the present invention causes air flow 46 through each typical impactor slot 16 to head toward a collection surface 28 that is wider than the length of impactor slots 16, and this results in a slowing down of the air flow near the center of each impactor slot 16. This is illustrated in FIG. 6 by arrows of unequal length, symmetrically disposed about the center of a typical impactor slot 16 and collectively identified by the numeral 46. As persons skilled in the art will immediately appreciate, the consequence of a downward flow of air through a typical impactor slot 16 toward a closely adjacent surface such as impact collection surface 28 is to cause an increase in flow resistance toward the center of the impactor slot between the lower surface of inlet element 12 and impactor surface 28. As a consequence, only relatively large particles 40 impact the central area of collection surface 28 and are collected thereon while some of the smaller particles are collected on the surface of 14 near the edges of exhaust aperatures 22 and away from the central area of 14. To each side of collection surface 28 the diverted air flow (indicated by curved arrows) entrains the smaller particles and carries them through exhaust apertures 22. As with the prior art, as the air flow is turned to pass the ends of impactor slots 16 and incidental centrifugal acceleration is imposed on the larger particles, tending to throw them toward surface 28 of impactor plate 14 while the lighter particles 42 continue entrained in the air flow and tend to follow the streamlines through exhaust apertures 22.

The air flow through exhaust apertures 22 is a divergent one as indicated by curved arrows in FIG. 6. This flow through exhaust apertures 22 slows down and distributes itself across the region beneath impactor plate 14 and the upper surface of filter element 48. As a direct result of this slowing down and redistributing of the air flow after passage through the divergent exhaust apertures 22, the flow through filter element 48 is relatively slow and results in a generally even distribution of the finer particles 42 on filter element 48. The air flow 60 having passed filter element 48, and through the openings in stainless steel screen 50, passes downward between inwardly tapering walls 56 and downward walls 58 for rejection through the ambient atmosphere or as desired.

To summarize the distinctions and the advantages obtained by the geometry as taught herein over the closest prior art geometry for comparable elements, it must be noted that by providing the inlet air flow through a plurality of relatively narrow elongate impactor slots 16 to a relatively large collection surface 28 of impactor plate 14 a nonuniform velocity distribution in the streamwise direction is obtained which tends to deposit the larger particles with varying efficiency along the length of impactor slots 16 on impactor surface 28, and the further provision of divergent elongate exhaust apertures 22 in impactor plate 14 slows down and distributes the air flow with entrained small particles 42 over a filter element 48 supported on a wire mesh screen 50 of conventional construction. Because the impactor collection surface 28 has a lateral dimension W that exceeds length V of impactor slots 16, by judicious selection of height H of the undersurface of inlet element 12 above impactor surface 28 it becomes possible to obtain the optimum nonuniform velocity distribution 46 for a selected operational flow rate through the sampler, with the intended advantage of effective separate collection on surface 28 of the larger particles 40, e.g., particles larger than 10 microns according to the human thoracic collection system, from the incoming air flow. The deliberate divergence of the air flow with smaller entrained particles 42 through elongate exhaust apertures 22 thereafter effects a uniform distribution of the finer particles 42 over filter element 48.

Naturally, as persons skilled in the art of fluid dynamics and particle mechanics will immediately appreciate, the desired air flow will determine various dimensions discussed herein, the number of impactor slots 16, the type and rating for filter element 48, and the like. Also important in this respect are other parameters such as ambient temperature and relative humidity which are bound to be different, depending on the location and weather where the air sampler is used. In brief, because numerous such operational parameters have to be considered by a designer and a user for a particular sampling operation, it may become highly desirable to vary certain geometric parameters of the combination taught herein.

Although not discussed in detail and not illustrated in FIG. 6 for the sake of simplicity, it will be appreciated by persons skilled in the art that the different components may be held together by clamping, bolting, or other conventional means and that such means may be selected to have the flexibility to accommodate changes in the geometric dimensions of the various elements that coact together. Thus, for a given inlet element 12, in order to accommodate to lower air flows, it should be relatively simple for a person skilled in the art to block off one or more impactor slots 16, or to replace a given inlet element 12 by a different inlet element 12 having a different dimension H, or to replace a given impactor plate 14 by a different impactor plate 14 having exhaust apertures 22 of a different width S, a collection surface 28 of a different length Z, or differently diverging exhaust apertures 22 having different values of the angle $\alpha$ or to replace a given spacer 52 by another spacer of a different thickness or a different width, or the like. In other words, depending on the particular exigencies of a given application, a user can adapt the disclosed combination with great freedom and a manufacturer of such elements may find it worthwile and profitable to provide a range of components that are all capable of coacting together in different combinations within the scope of the invention disclosed herein.

It is believed that a nonuniform velocity distribution through the impactor slots 16, which can be altered by selection of different widths U and different lengths V for these apertures, by itself provides a ready control over the size distribution of particles that are collected on impactor collection surface 28 therebelow. This controlled nonuniform velocity distribution, deliberately obtained by disposing impactor slots 16 orthogonal to more widely spaced apart elongate exhaust apertures 22 in the impactor plate, results in a unique, nonobvious and highly versatile collection mechanism for separating out particulate matter having aerodynamic diameters greater than, for example, 10 microns according to the thoracic system.

As will be appreciated by persons skilled in the art, the relatively large size of the impactor collection surface 28 permits collection over a prolonged period which experimental evidence indicates may be as long as four weeks. As is well known in the art, the collection surface 28 may be coated with an appropriate adhesive, e.g., petrolatum or Vaseline TM, that may subsequently be rinsed off with a solvent such as chlorothene TM, for recovery of the collected dust for further analysis and assay thereof. Because the collection surface 28 according to the present invention is relatively large, the very act of coating it with an adhesive is made much easier and more convenient than is the case with the narrow surfaces as taught in the prior art (best illustrated in FIG. 5).

Because the important components of the present combination are easily separable, contact between adjacent parts being effected at smooth planar surfaces only, it is relatively easy even for unskilled personnel using simple tools to extract impactor plate 14 and filter element 48 from the disclosed assembly for replacement thereof for a further sampling activity.

The method for using the present invention is relatively straightforward and simple. A clean impactor plate 14 is coated with a suitable adhesive over its principal large particle collecting surface 28 and is bolted to a suitable inlet element 12. The two of them in combination are then placed over a fresh unused filter element 48 with a spacer 52 therebetween, and the assembly is bolted, clamped or otherwise completed for use. The combination according to FIG. 6 is then utilized with a conventional air sampling system in which particulate laden air is directed through impactor slots 16 as described hereinabove. The avoidance of cyclone separators, electric motors to turn collection surfaces, more complex assemblies, frangible outside containers, and other such disadvantages of the prior art make the present invention relatively simple and easy to use. After a suitable period of operation, the collected dust may be removed on the impactor plate 14 (larger particles) and filter element 48 (smaller particles). The various disassembled elements may be readily cleaned with a solvent and reused repeatedly.

It is anticipated that persons skilled in the art, armed with the knowledge provided by this disclosure, will contemplate a variety of modifications in the structure and uses of this invention. All such modifications and variations are expressly contemplated as being encompassed within the claims appended below.

What is claimed is:

1. A particle impactor assembly, for use in a high volume air sampler apparatus for collecting and separating by size, entrained particles from sampled air, comprising:
   a. an inlet element formed to have a horizontal and substantially flat upper portion with a plurality of similar elongate parallel through impactor slots, each having a length V and a width U, said upper portion having:
      (1) a downwardly depending peripheral rim of height H, having inner vertical surfaces, and
      (2) a distance R between each impactor slot end and the nearest rim portion normal to said impactor slot end, such that the separation between the inner vertical surfaces of said rim portion extending parallel to said length V equals at least (V+2R);
   b. an impactor plate having an upper surface sealingly affixable to a lowermost part of said rim of said inlet element, the impactor plate being formed to have two similar elongate parallel through exhaust apertures symmetrically oriented normal to the impactor slots thereabove, said exhaust apertures being separated by a distance of at least (V+2U) and each said exhaust aperture at the upper surface having a width S and a length extending past the corresponding last adjacent impactor slot by a distance of at least 2U, for impaction thereon of at least the larger particles entrained in the air flow, whereby the velocity distribution in the air flow through said impactor slots is non-uniform and has low velocities near a central portion of said impactor slots for promoting the impaction of larger particles only and the collection of both larger and smaller particles on said impactor surface below said impactor slots, where air flows through said apertures; and
   c. means for affixing said inlet element to said impactor plate.

2. A particle impactor assembly according to claim 1, wherein:
   said exhaust apertures diverge through the thickness of said impactor plate.

3. A particle impactor assembly according to claim 2, wherein:
   said diverging exhaust apertures have lengthwise inclined surfaces disposed at a predetermined angle $\alpha$ to a local normal to said impactor plate upper surface.

4. A particle impactor assembly according to claim 3, wherein:

$$\alpha = 45°.$$

5. A particle impactor assembly according to claim 1, wherein:
   said impactor plate upper surface, at least between said exhaust apertures, is coated with an adhesive material to facilitate collection thereby of said particles impacting thereon.

6. A particle impactor assembly according to claim 5, wherein:
   said adhesive is separable from said collected particles by a solvent.

7. A particle impactor assembly according to claim 6, wherein:
   said dissolvable adhesive comprises petrolatum.

8. A particle impactor assembly according to claim 6, wherein:
   said dissolvable adhesive comprises a heavy oil.

9. A particle impactor assembly, according to claim 1, wherein:
   said distance R is at least equal to said width U of said inlet slots.

10. A particle impactor assembly according to claim 1, further comprising:
    a peripheral spacer element sealingly affixable to a lower surface of said impactor plate.

11. A particle impactor assembly according to claim 10, further comprising:
    filter means, sealingly affixed to a lower surface of said spacer element for disposition substantially parallel to said lower surface of said impactor plate, for filtering fine particulates entrained in air flowing through said exhaust apertures.

12. A particle impactor assembly according to claim 11, wherein:
    said filter means comprises a fine filter element selected to filter out particles within a predetermined size range.

13. A particle impactor assembly according to claim 12, wherein:
    said filter means further comprises a filter element support means for supporting said fine filter element thereon, said support means being foraminous to enable ready flow of filtered air flow therethrough.

14. A particle impactor assembly according to claim 4, wherein:
    said impactor plate upper surface, at least between said exhaust apertures, is coated with an adhesive material to facilitate collection thereby of said particles impacting thereon.

15. A particle impactor assembly according to claim 14, wherein:

said adhesive is separable from said collected particles by a solvent.

16. A particle impactor assembly according to claim 15, further comprising:

a peripheral spacer element sealingly affixable to a lower surface of said impactor plate; and filter means, sealingly affixed to a lower surface of said spacer element for disposition substantially parallel to said lower surface of said impactor plate, for filtering fine particulates entrained in air flowing through said exhaust apertures.

17. A method for sampling particulate matter entrained in a directed air flow, such that particles larger than a predetermined characteristic size are collected separately from smaller particles according to the thoracic cut, comprising the steps of:

a. directing the particulate-laden air flow downwardly through a plurality of similar elongate, parallel impactor slots of a first length V and a first width U;

b. diverting said particulate-laden air flow coming through said impactor slots by an impactor surface disposed a predetermined distance therebelow, the air flow being then directed through two elongate, parallel exhaust apertures in said impactor plate, the exhaust apertures being separated by a distance of at least (V+2U) and being oriented normal to the impactor slots whereby the velocity distribution in the air flow through said impactor slots is non-uniform and has low velocities near the centers thereof for promoting only the impaction and collection of the larger of said particles on a central area of said impactor surface; and c. filtering the air directed through said exhaust apertures by passage thereof through a filter to collect the finer of said particles separately thereby.

18. A method according to claim 17, further including the step of:

diverging the air flow through said exhaust apertures to slow down the same and to uniformly distribute the collection of said filtered fine particles.

19. A method according to claim 18, further including the step of:

coating said impactor surface with an adhesive material.

20. A. method according to claim 17, further including the steps of:

periodically removing collected particles from said impactor surface and from said filter.

* * * * *